United States Patent [19]

Bendix et al.

[11] Patent Number: 4,810,775

[45] Date of Patent: Mar. 7, 1989

[54] PROCESS FOR PURIFYING RESORBABLE POLYESTERS

[75] Inventors: Dieter Bendix; Dieter Reichert, both of Ingelheim am Rhein; Michael Scharfe, Wiesbaden, all of Fed. Rep. of Germany

[73] Assignee: Boehringer Ingelheim KG, Ingelheim am Rhein, Fed. Rep. of Germany

[21] Appl. No.: 170,188

[22] Filed: Mar. 18, 1988

[30] Foreign Application Priority Data

Mar. 19, 1987 [DE] Fed. Rep. of Germany ....... 3708916

[51] Int. Cl.$^4$ ............................................. C08F 6/12
[52] U.S. Cl. ................................... 528/480; 528/481; 528/486; 528/487; 528/491; 528/492; 528/493; 528/494; 528/496; 528/497; 528/499; 528/502; 528/503; 210/768; 210/772; 210/773; 210/774; 210/787

[58] Field of Search ............... 528/480, 481, 486, 487, 528/491, 492, 493, 494, 496, 497, 499, 502, 503; 210/768, 772, 773, 774, 787

[56] References Cited

U.S. PATENT DOCUMENTS

| | | | |
|---|---|---|---|
| 3,297,033 | 1/1967 | Schmitt et al. | 128/335.5 |
| 3,878,284 | 4/1975 | Schmitt et al. | 264/184 |
| 4,279,249 | 7/1981 | Vert et al. | 128/92 D |
| 4,313,879 | 2/1982 | Klenk et al. | 260/343 |
| 4,341,709 | 7/1982 | Hofen et al. | 549/272 |
| 4,454,045 | 6/1984 | Perplies | 210/672 |
| 4,523,591 | 6/1985 | Kaplan et al. | 128/334 R |

Primary Examiner—John Kight
Assistant Examiner—S. A. Acquah
Attorney, Agent, or Firm—David E. Frankhouser; Alan R. Stempel; Mary-Ellen M. Timbers

[57] ABSTRACT

The invention relates to the purification of polymers, particularly resorbable polyesters, using shear fields produced mechanically or by fluid dynamics.

23 Claims, 2 Drawing Sheets

PROCESS FOR PURIFYING RESORBABLE POLYESTERS

The invention relates to a process for purifying polymers, prticularly resorbable polyesters.

The manufacture and use of resorbable polyesters is known from the prior art, for example German Offenlegungsschriften Nos. 12 93 396, 15 95 085, 17 20 211, 21 18 127, 22 06 144, 25 01 448, 27 00 729, 28 25 911, 28 27 289, 28 50 824, European patent application Nos. 73 655, 98 394, 102 265, 108 933, 176 895 etc.

As is already known from numerous publications, the major advantage of resorbable polyesters, particularly those based on lactic or glycolic acid, is the fact that they are broken down completely in human or animal tissue or in human or animal liquids to form compounds which occur naturally in the body, whilst the breakdown rate of the polymer may be varied, depending on the intended purpose, from a few hours to several months. The breakdown products pass into the normal biochemical metabolism and are either eliminated directly or eventually metabolized to form water and carbon dioxide.

In recent years, interest in the use of resorbable polyesters has increased sharply, for example in the field of surgery, for use as suture material or clamps, and in the field of osteosynthesis as a substitute for metal implants.

The use of resorbable polyesters in galenic preparations with a sustained or controlled release of active substance in order to produce sustained or controlled release forms and implants is of particular interest.

By varying the monomers and comonomers, the molar ratios, the reaction conditions, the nature and quantity of one or more catalysts and the addition of regulators, it is possible to produce the optimum polyesters for a variety of applications. Owing to the fact that these resorbable polyesters are specifically used in human or animal bodies, it is essential or at least desirable to use only those polyesters which are free from any impurities which might possibly cause irritation. Such impurities would include, for example, unreacted residual monomers, molecular weight regulators and polymerization catalysts.

The physical structure of the polyesters may be crystalline, partly crystalline or completely amorphous.

The crystallinity of polyesters may be assessed according to various criteria (see for example U.S. Pat. No. 4,523,591 and U.S. Pat. No. 3,878,284), but preferably by plotting DSC (differential scanning calorimetry) curves. Partly crystalline or amorphous, resorbable polyesters are taken to be those which show only one glass transition in DSC. Crystalline polyesters will additionally show recrystallization and melting peaks, sometimes only after suitable pretreatment.

Partly crystalline or amorphous resorbable polyesters are particularly useful in the field of the controlled release of active substance, since they show shorter release times and faster decomposition in the body then crystalline polyesters.

Partly crystalline or amorphous resorbable polyesters of this kind may be prepared by solution, emulsion or bulk polymerization in a melt. The polyesters thus obtained must be purified in order to remove any residual monomers, oligomers, additives used to regulate molecular weight, catalysts and other impurities originating from the polymerization reaction.

For example, bulk polymers are purified by decocting the ground polyesters with a suitable solvent (U.S. Pat. No. 4,523,591). Usually, in order to remove the abovementioned impurities, polymers are dissolved in a suitable organic solvent, purified, possibly by filtration with activated charcoal additive, and recovered by the addition of a precipitating agent.

By contrast with crystalline polyesters, partly crystalline or amorphous polyesters cannot be isolated from their solutions in an organic solvent by the addition of a precipitating agent.

If, for example, one attempts to isolate the polymer by the addition of a precipitating agent or by adding the solution to a precipitating agent, the amorphous structure of the polymer will result only in a jelly-like mass containing large quantities of precipitating agent and solvent and incapable of being further processed. Nor can partly crystalline or amorphous polyesters be purified by recrystallization from a solvent or mixture of solvents.

The aim of the present invention is to provide a process for purifying partly crystalline or amorphous polyesters, particularly resorbable polyesters.

According to the invention, partly crystalline or amorphous polyesters are purified by dissolving the polymer in a suitable solvent or solvent mixture, then so contacting the polymer solution with a precipitating agent that the polymer thus precipitated is broken up into minute particles by the shear forces occurring.

Obviously, this method may be also be used to advantage to purify crystalline polyesters, but they can also be purified by the methods described above.

German Patent No. 26 46 332 describes, for example, the preparation of fibrils of fluorine-containing polymers with the aid of dispersing machines or two-substance nozzles, whilst German Offenlegungsschrift 2 208 921 describes the preparation of short fibres of thermoplastic plastics by precipitation with the use of shear forces.

It has now surprisingly been found that crystalline, partly crystalline or amorphous polyesters, particularly resorbable polyesters, prepared from solutions thereof by these methods, are substantially free from impurities such as catalysts, residual monomers, etc. Suitable polyesters according to the invention are those which are soluble in an organic solvent or mixture of solvents, if necessary after suitable pretreatment, e.g. temperature adjustment. The cyrstallinity of the polyesters is preferably between zero and seventy, more particularly between zero and twenty percent.

Homo- and co-polymers based on hydroxycarboxylic acids, such as polymers of glycolide, lactide, methylglycolide, dimethylglycolide, polymethylglycolide, diethylglycolide, dibutylglycolide, caprolactone, valerolactone, decalactone, propiolactone, butyrolactone and pivalolactone as well as polymers based on trioxanone (1,3 and 1,4), dioxanone (1,3 and 1,4), substituted dioxanone, trimethylenecarbonate, ethylenecarbonate and propylenecarbonate are preferred.

Other suitable comonomers include the following compounds: lactic acid, glycolic acid, pentaerythritol, sorbitol, adonitol, xylitol, fructose, epichlorohydrin, isopropyl-morpholine, isopropylmethylmorpholinedione, beta-propiolic acid, tetramethyl glycolide, beta-butyrolactone, gamma-butyro-lactone, pivalolactone, alpha-hydroxybutyric acid, alpha-hydroxyisobutyric acid, alpha-hydroxyvaleric acid, alpha-hydroxyisovaleric acid, alpha-hydroxycaproic acid, alpha-hydroxyisocaproic acid, alpha-hydroxy-alpha-ethylbutyric acid, alpha-hydroxy-alpha-methylvaleric acid, alpha-hydroxyheptanoic acid, alpha-hydroxyoctanoic acid, alpha-hydroxydecanoic acid, alpha-hydroxytetradecanoic acid and alpha-hydroxystearic acid.

Homopolymers of lactide, copolymers of different lactides and copolymers of lactides and glycolide with inherent viscosities of between 0.1 and 10 dl/g are particularly preferred.

The lactide used may be L-, D-, meso- or D,L-lactide or mixtures thereof.

Also preferred are homopolymers of D,L-lactide with an inherent viscosity of 0.1 to at least 6 dl/g, corresponding to average molecular weights of 2000 to at least 2 million, calculated from the inherent viscosity by approximation of the Staudinger index according to Solomon and Ciuta (see. J. Apply. Polym. Sci., 6.24 (1962) 683–6) and putting into the Mark-Houwink equation the parameters K=6.06 E-4 and a=0.64 (see. J. Rak, J. L. Ford, Ch. Rostron and V. Walther, Pharm. Acta Helv., 60, 5–6 (1985) 162–9). Copolymers of L-lactide and glycolide are also preferred having inherent viscosities up to at least 4.5 dl/g. Using the method described above and the Mark-Houwink parameters K=5.45 E-4 and a=0.73 (see. S. Gogolewski and A. J. Pennings, J. Appl. Polym. Sci., 28, 1045–61) average molecular weights of from 50,000 to at least 250,000 are calculated.

Other preferred copolymers are those of D,L-lactide and glycolide with inherent viscosities of at least 2.5 dl/g, corresponding to average molecular weights of at least 110,000, calculated using the above Mark-Houwink parameters for copolymers; also copolymers of epsilon-caprolactone with L-, D,L-lactide and glycolide and inherent viscosities of up to at least 4 dl/g; also poly(L-lactide-co-DL-lactide) in the ratio 9:1, poly(L-lactide-co-glycolide) in the ration 7:3, poly(D,L-lactide-co-glycolide) in the ratio 3:1, poly(D,L-lactide-co-glycolide) in the ratio 1:1, poly(D,L-lactide-co-glycolide) in the ratio 45:55. (The figures given are molar ratios).

For example, homopolymers and copolymers of lactic and glycolic acid are preferably prepared by ring-opening polymerisation of the cyclic diesters of lactic and glycolic acids, namely the lactide and glycolide.

Owing to the chirality of lactic acid, the optically active L- and D-lactides and the optically inactive mesolactide and the racemate (D,L-lactide) may be included in the ring-opening polymerization.

The conditions of this polymerization are known. The homopolymers are prepared in solution or emulsion or in a melt. The copolymers of any desired composition may be prepared in emulsion owing to the different reactivities of the comonomers but are preferably prepared by bulk polymerization in a melt. During the polymerization, the desired molecular weight and the corresponding molecular weight distribution may be achieved by varying the reaction parameters of temperature, time and catalyst concentration and by adding one or more co-catalysts.

In order to perform the purification process, the crystalline, partly crystalline or amorphous polyesters prepared by known methods are dissolved in a suitable organic solvent or a mixture of different organic solvents. Any organic solvent which adequately dissolves the polyester in question and which is miscible with the precipitation agent chosen in the mixing ratio under consideration is a suitable solvent.

Preferred solvents are acetone, 1,4-dioxan, dimethylacetamide, tetrahydrofuran, toluene, methylformamide, dimethylsulphoxide or chlorinated hydrocarbons such as chloroform or methylene chloride.

If it seems necessary, the actual precipitation may be preceded by additional purification stages, such as filtering with the addition of activated charcoal. The polyester is then precipitated from the polymer solution in the presence of a precipitation agent, whilst a shear field is produced by a dispersing unit. A precondition for this is that the solvent and precipitation agent must mix together completely within the area of the composition in question.

The precipitation agent used may be, for example, water to which small amounts of an inorganic or organic acid, an inorganic or organic base, agents for varying the surface tension or a complexing agent may be added in order to achieve particular, additional purifying effects. Other suitable precipitation agents are methanol, ethanol, freons, hydrocarbons and hydrocarbon mixtures such as petroleum ether, and organic solvents which are a nonsolvent for the polyester.

It is advantageous if the precipitation agent has a higher boiling point and lower volatility than the solvent. If chloroform or methylene chloride is used as solvent, the preferred precipitation agents are hexane, petroleum ether or a freon.

If acetone, dimethylacetamide, dioxan, tetrahydrofuran, dimethylformamide or dimethylsulphoxide or mixtures thereof are used as solvent, the preferred precipitation agent is water. The temperature of the components involved is generally between $-20°$ C. and the boiling point of the solvent mixture, preferably between $-20°$ C. and ambient temperature. Dispersion of the organic polymer solution in the precipitation agent can be produced by a mechanical dispersing unit. Dispersing units of this kind generate, by means of tools rotating at high speed, a correspondingly large shear field. Standard commercial machinery, e.g. the Super Dispax SD40, may be used, i.e. the turbulent shear field is produced by an apparatus consisting essentially of a stator and a rotor moving relative to this stator. The polymer solution is conveniently metered into the inlet to the apparatus in such a way that the polymer solution is introduced directly from the supply means into the shear field produced by the rotor and stator.

BRIEF DESCRIPTION OF THE DRAWINGS

Continuous operation can be achieved, for example, with the following apparatus (see FIG. 1): From a container (1) the contents of which are stirred in order to avoid any inhomogeneity, the polymer solution is fed by a metering pump (2) through a narrow tube directly over the mechanical dispersing unit (3) and immediately distributed very finely in the circulating precipitation agent under the effect of the mechanically produced shear field. By the pumping action, the dispersing unit conveys the mixture of polymer and precipitation agent into a receiving container (4) which is cooled in order to dissipate the heat introduced during the dispersing process. The polymer is separated off by means of a suitable screen (5). The precipitation agent is pumped back out of the container by means of a pump (6) through a safety filter (7) into the storage container (8) of the dispersing unit. Since there is a build-up of solvent in the precipitation agent when this procedure is used, the precipitation agent must be changed when the solvent/precipitation agent system reaches a certain concentration. The solvent can be recovered if necessary, e.g. by distillation.

In another alternative embodiment of the process, a two-substance nozzle (see FIG. 2) is used instead of a mechanical dispersing unit. The polymer solution is forced out of a pressurised container through the inner bore (9) of the nozzle, whilst the precipitation agent is pumped at high speed through the outer, concentrically arranged annular channel (10). Immediately after leaving the nozzle, the central stream (polymer solution) is turbulently mixed with the concentric stream (precipitation agent) coming out in the form of a hollow cone. As a result of the high differences in velocity of the two media and the resulting shear action, the polymer solution is dispersed in the precipitation agent. The arrangement of the nozzle on the base of a vertically positioned cylinder filled with precipitation agent means that the polymer fibrils precipitated float to the surface of the large excess of precipitation agent and can be removed. A continuously operating apparatus which makes use of this nozzle is shown in FIG. 3. The polymer solution is forced out of a stirrer mechanism (11) by the application of a nitrogen overpressure through the inner bore of the nozzle (12), whilst at the same time the precipitation agent is pumped out of a storage container (13) through a heat exchanger (14) and through the outer annular channel of the nozzle by means of a pump (15). Through the outlet (16) of the vertically positioned precipitation cylinder (17), the mixture of polymer and precipitation agent is fed into a centrifuge (18) operating at low speed. The precipitation agent running out is pumped back into the storage container (13). Since this procedure causes a build-up of solvent in the precipitation agent, the precipitation agent must be changed when the concentration of solvent in the solvent/precipitation agent system reaches a certain level. The solvent may be recovered if necessary, e.g. by distillation.

Figure 1:
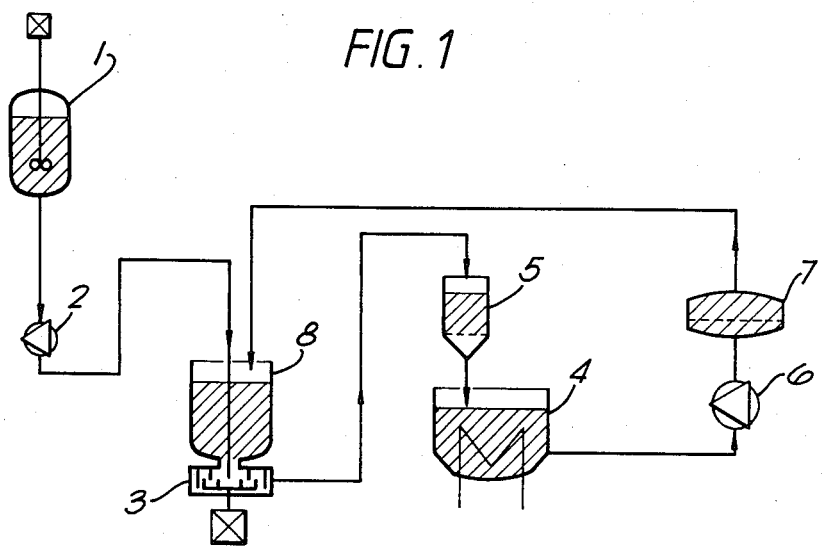
Figure 3:
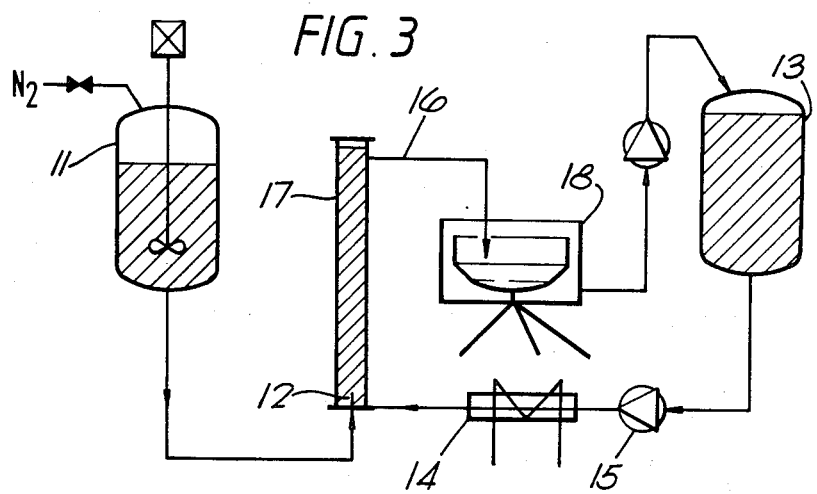
Figure 2:
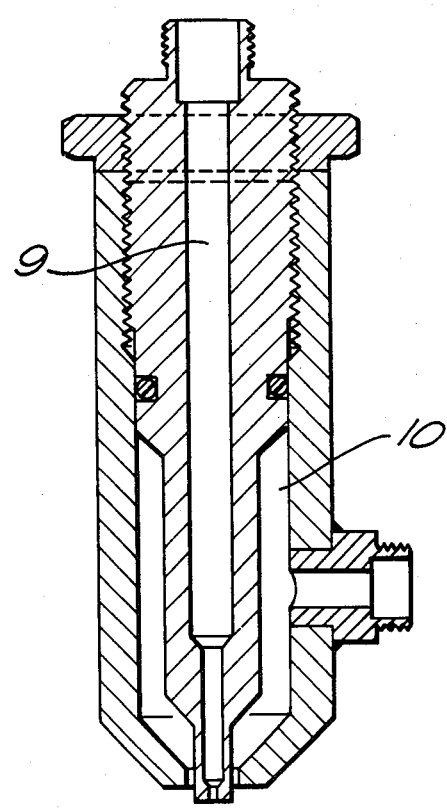

Instead of the centrifuge, it is also possible to use a suction filter (pressurized suction filter), an infusion filter, a continuously operating belt filter or a continuously operating screw press.

The crystalline, partly crystalline or amorphous resorbable polyesters thus obtained occur in the form of thread-like or felt-like fibrils after drying and may be homogenized by grinding with the addition of a refrigerant such as dry ice or liquid nitrogen.

The polyesters purified according to the invention are particularly suitable for the manufacture of objects which are capable of being resorbed in the human or animal body.

These include, in particular, objects for use in osteosynthesis and carriers for pharmaceutical active substances. The latter may, for example, be in the form of tablets or capsules but may also take the form of implantable or injectable sustained or controlled release forms.

The following are some typical products for medical use which may advantageously be made from resorbable polymers. Products made from resorbable polymers:

1. Solid products, compression moulded or machined:

Orthopaedic pins, clamps, screws and
plates, clips (e.g. for vena cava),
staples,
hooks, buttons or press-studs,
bone replacements (e.g. jaw prostheses),
needles,
non-permanent intrauterine inserts (spermicidal),
temporary drainage or exploration tubes or
capillaries,
surgical instruments,
blood vessel implants or supports,
vertebrae,
extracorporeal tubes for kidney and heart-lung machines,
slowly disintegrating ion exchange resin,
slowly disintegrating products which release active substances (pills, pellets), reinforced bone pins, needles etc.,
implantable pellets, sticks, films and other shaped objects charged with pharmaceutical compositions for the controlled release of active substance.

2. Fibre products, knitted or woven, including velour
burn bandages,
fracture pads,
absorbent paper or swabs,
medicinal dressings,
items used in plastic surgery,
gauze, tissue, cloth, felt or sponge for haemostasis,
gauze bandages,
dental fillings,
suture material including ligatures.
Arterial transplants or replacements,
bandages for the surface of the skin,
burn dressings (combined with other polymer films).

3. Powdered products produced by spray drying, grinding, precipitation or microencapsulation.

Injectable or implantable powder charged with drugs for the controlled and delayed release of the active substance. Microporous shaped objects, films, powders and granules for charging with active substances.

4. Miscellaneous

Flakes or powders for treating burns or abrasions, foam as an absorbable prosthesis, substitutes for wire in splints, film spray for prosthetic elements and for

EXAMPLES

Example 1

16.2 g of a poly(D,L-lactide-co-glycolide) 50:50 mol % crude product are dissolved in 81 ml of acetone. Petroleum ether is placed in a standard kitchen mixer under a nitrogen blanket. The mixer is switched on and the polymer solution is slowly added dropwise through a dropping funnel. The polymer which is precipitated in thread-like form by the dispersing action of the mixer is continuously sucked out of the mixing bowl and the precipitation agent is continuously replaced from a second dropping funnel.

The mixture of polymer and precipitation agent sucked out is suction filtered and the polymer is dried in a circulating air dryer at 40° C.

Yield: 12.2 g, 75% of material put in Inherent viscosity: 0.35 dl/g (chloroform, 25° C.)

Example 2

18.1 g of a poly(D,L-lactide-co-glycolide) 50:50 mol % crude product are dissolved in 90 ml of acetone. As described in Example 1, the polymer is precipitated with water as the precipitation agent and dried.

Yield: 21.3 g, 99% of the material put in Inherent viscosity: 0.39 dl/g (chloroform, 25° C.)

Example 3

816.6 g of a poly(D,L-lactide-co-glycolide) 50:50 mol % crude product are dissolved in 4 l of acetone. The hot solution is mixed with 10 g of Carboraffin C and 10 g of Clarcel and filtered through a pressure filter. After cooling, the solution is taken out of a stirred storage vessel and by means of a metering pump injected through a metal capillary directly above the mechanical dispersing unit of a Super-Dispax SD40 operating at high speed into water as the precipitation agent. The polymer is immediately precipitated as a fine, thread-like material. The pumping action of the Dispax conveys the mixture of polymer and precipitation agent into a 100 liter tank. In order to dissipate the heat formed by the dispersing, the tank is acted upon with cooling water in a double jacket. The floating polymer becomes matted on the surface of the water and can be skimmed off with a sieve. The polymer, which still contains a very large quantity of precipitaction agent and hence some solvent, although in smaller quantities, is washed with cold water, exhaustively suction filtered and dried in a circulating air dryer at 40° C.

The precipitation agent is sucked up again from the base of the tank by means of a pump and after any fine components have been separated off using a Scheibler filter it is pumped back into a storage container of the Dispax. The entire quantity of polymer can be worked up without changing the precipitation bath (concentration of acetone in the water after precipitation: 5%).

Yield: 700 g, 86% of material put in Inherent viscosity: 0.39 dl/g (chloroform, 25° C.) Water content: 0.51% after Karl-Fischer titration Residual monomer: 0.1% by weight of D,L-lactide, less than 0.03% by weight of glycolide

Example 4

1018.8 g of poly(D,L-lactide-co-glycolide) 75:25 mol % crude product are dissolved in 5 l of acetone. The solution is worked up as described in Example 3. The total quantity of polymer can be worked up without changing the precipitation bath (concentration of acetone in the water after precipitation: 6.3%).

Yield: 965 g, 95% of the material put in Inherent viscosity: 0.72 dl/g (chloroform, 25° C.) Water content: 0.64% after Karl-Fischer titration Residual monomer: 0.15% D,L-lactide; 0.15% by weight of glycolide

Example 5

990 g of poly(D,L-lactide) crude product are dissolved in a total of 12 l of acetone. The solution is worked up as described in Example 3. The total quantity of polymer can be worked up without changing the precipitation bath (concentration of acetone in the water after precipitation: 15%).

Yield: 938 g, 95% of the material put in Inherent viscosity: 2.11 dl/g (chloroform, 25° C.) Water content: 0.38% after Karl-Fischer titration Residual monomer: 0.5% by weight

Example 6

100 g of a poly(D,L-lactide-co-glycolide) 50:50 mol% crude product are dissolved in 1 liter of acetone. The solution is transferred into a pressurized container and the contents of the container are forced through the inner channel (diameter 0.7 mm) of a two-substance nozzle with an overpressure of about 3 bar. At the same time, water is pumped through the outer segment of the two-component nozzle with a throughput of about 50 l/min by means of a pump. The two streams emerge into a vertical cylinder (precipitation tube) filled with precipitation agent, at which point the shearing and turbulence occurring bring about dispersion of the polymer solution and precipitation of the polymer.

The outlet from the precipitation tube leads into a water-filled 100 liter rim boiler with double jacket cooling. The floating polymer can be picked up from the surface of the water using a sieve. The polymer which still contains a very large quantity of precipitation agent and hence some solvent, although in small amounts, is washed with cold water, exhaustively suction filtered and dried in a circulating air dryer at 40° C. The precipitation agent is sucked up from the base of the rim boiler and fed back into the two-component nozzle. The entire quantity of polymer can be worked up without changing the precipitation bath. (Concentration of acetone in the water after precipitation: 1.5%).

Yield: 93.8 g, 94% of the material put in Inherent viscosity: 2.08 dl/g (chloroform, 25° C.) Water content: 0.37% after Karl-Fischer titration

Example 7

1.730 kg of a poly(D,L-lactide-co-glycolide) 75:25 mol % crude product are dissolved in 17 l of acetone. The solution is transferred into a pressure filter and forced through the inner channel of the two component nozzle with a nitrogen overpressure of about 3 bar. At the same time, the precipitation agent, namely water, is pumped through the outer segment of the two component nozzle with a throughput of about 50 l/min by means of a pump. The two streams emerge into a vertical cynlinder filled with precipitation agent, whilst the shearing and turbulence which then occur bring about dispersion of the polymer solution and precipitation of the polymer. The overflow from the precipitation tube leads into a pressureless pressure filter, and the hydrostatic pressure causes the water to flow back down into a receiving container placed underneath. From here, it is pumped through a tube in the form of a heat exchanger, cooled with brine, back through the two-component nozzle.

After precipitation has ended, the pressure filter is exposed to nitrogen and the residual water is thoroughly forced out, the polymer is washed with cold water and again the water is thoroughly forced out. The polymer is then dried in a circulating air dryer at 40° C.

Yield: 1.68 kg, 97% of the material put in The dried polymer is mixed with dry ice, ground on an Alexander grinder with a 0.6 mm slanting hole screen and then dried in a circulating air dryer at 40° C.

Yield: 1.64 kg, 98% of the material put in Inherent viscosity: 0.68 dl/g (chloroform, 25° C.) Water content: 0.43% after Karl-Fischer titration Residual monomer: less than 1% by weight.

Example 8

0.770 kg of a poly(D,L-lactide) crude product is dissolved in 20 liters of 1,4-dioxan. The polymer solution is worked up as described in Example 7. The still moist product is mixed with dry ice and after being thoroughly frozen, ground using a pre-cooled Condux cutting mill.

Yield: 0.70 kg, 78% of the material put in Inherent viscosity: 3.2 dl/g (chloroform, 25° C.) Water content: 0.35% after Karl-Fischer titration Residual monomer: none detectable Sn content: 34 ppm (138 ppm used in the catalyst)

Example 9

24.8 kg of poly(D,L-lactide) crude product are dissolved in about 240 l of acetone in a 250 l stirrer apparatus. The contents of the apparatus are transferred in batches into a 60 l pressurized filter and precipitated with water as the precipitation agent as described in Example 7. The overflow from the precipitation tube is this time fed into a slowly rotating centrifuge. The water drained off is recirculated as described. After precipitation has ended the number of revolutions of the centrifuge is increased, the precipitation agent adhering is centrifuged off as much as possible, the polymer in the centrifuge is washed three times with cold water and after the centrifuge has been removed it is dried in a circulating air dryer at 40° C. The polymer is then homogenized with the addition of dry ice by grinding on an Alexander grinder.

Yield: 21.6 kg, 87% of the material put in Inherent viscosity: 0.93 dl/g (chloroform, 25° C.) Water content: 0.36% after Karl-Fischer titration Residual monomer: none detectable Example 10

Approximately 4 kg of a poly(D,L-lactide-co-glycolide) 50:50 mol% crude product were dissolved in dioxan as in Example 7 and precipitated from water using a two component nozzle.

| Batch No. | Residual monomer content (% by weight) | | Sn content (ppm) | |
|---|---|---|---|---|
| | Crude product | End product | Crude product | End product |
| 1 | 5.3 | less than 0.1 | 75.5 | none detectable |
| 2 | 3.8 | less than 0.1 | 75.5 | 9 |
| 3 | 2.7 | less than 0.1 | 50 | 3 |
| 4 | 12.4 | less than 0.1 | 25 | none detectable |

Example 11

4 kg of a poly(D,L-lactide-co-glycolide) 75:25 mol% crude product were dissolved in dioxan as in Example 7 and precipitated from water using a two component nozzle.

| Residual monomer content (% by weight) | | Sn content (ppm) | |
|---|---|---|---|
| Crude product | End product | Crude product | End product |
| 3.7 | less than 0.1 | 137.5 | 11 |

What is claimed is:

1. A process for the purification of polymers, characterized in that the polymer is dissolved in a solvent and the polymer solution is subsequently brought into intimate contact with a precipitation agent under the effect of high shear forces in a turbulent shear field, so that the polymer precipitated is divided up into minute particles.

2. The process as claimed in claim 1, further characterized in that the polymer to be purified is a resorbable polyester which is a polymer or copolymer based on L-lactide, D-lactide, D,L-lactide, meso-lactide, glycolide and/or caprolactone.

3. The process as claimed in claim 2, further characterized in that the crystallinity of the polyester is between zero and 70%.

4. The process as claimed in claim 3, further characterized in that the crystallinity of the polyester is between zero and 20%.

5. The process as claimed in claim 1, further characterized in that the precipitation agent is an organic solvent.

6. The process as claimed in claim 1, further characterized in that the precipitation agent is water.

7. The process as claimed in claim 1, further characterized in that the precipitation agent consists of a mixture of several solvents.

8. The process as claimed in claim 1, further characterized in that the precipitation agent consists of a mixture of several solvents and water.

9. The process as claimed in claim 1, further characterized in that a complexing agent, an acid or a base or an adjuvant for altering the surface tension is added to the precipitation agent.

10. The process as claimed in claim 1, further characterized in that the solvent is acetone, dimethylacetamide, dioxan, tetrahydrofuran, dimethylformamide or dimethyl-sulphoxide and the precipitation agent is water.

11. The process as claimed in claim 1, further characterized in that the solvent is chloroform or methylene chloride and the precipitation agent is hexane, petroleum ether or a freon.

12. The process as claimed in claim 1, further characterized in that the temperature of the polymer solution or the precipitation agent or both is between ambient temperature and the boiling temperature of the solvent or precipitation agent.

13. The process as claimed in claim 1, further characterized in that the temperature of the polymer solution or precipitation agent or both is between ambient temperature and −20° Celsius.

14. The process as claimed in claim 1, further characterized in that the turbulent shear field is produced by an apparatus comprising of a stator and a rotor moving relative to this stator.

15. The process as claimed in claim 14, further characterized in that the polymer solution is metered into the inlet to the apparatus in such as a way that, immediately after being fed in, the polymer solution is introduced into the shear field generated by the rotor and stator.

16. The process as claimed in claim 1, further characterized in that the turbulent shear field is produced by an apparatus comprising of a two component nozzle and a container filled with precipitation agent into which the two component nozzle projects.

17. The process as claimed in claim 16, further characterized in that the polymer solution is forced through the narrow inner bore and the precipitation agent is forced through the outer annular channel of the nozzle.

18. The process as claimed in claims 14 or 16, further characterized in that the polymer precipitated is continuously separated from the precipitation agent with the aid of a centrifuge.

19. The process as claimed in claims 14 or 16, further characterized in that the polymer precipitated is continuously separated from the precipitation agent with the aid of a pressure suction filter.

20. The process as claimed in claims 14 or 16, further characterized in that the polymer precipitated is continuously separated from the precipitation agent with the aid of a belt filter.

21. The process as claimed in claim 1, further characterized in that the polymer to be purified is a resorbable polyester selected from the group comprising the homopolymers and copolymers based on hydroxycarboxylic acids, and polymers based on trioxanone (1,3 and 1,4), dioxanone (1,3 and 1,4), substituted dioxanone, trimethylene carbonate, ethylene carbonate and propylene carbonate and optionally contains as comonomer one or more compounds selected from the group comprising lactic acid, glycolic acid, pentaerythritol, sorbitol, adonitol, xylitol, fructose, epichlorohydrin, isopropylmorpholine, isopropylmethylmorpholinedione, beta-propiolic acid, tetramethylglycolide, beta-butyrolactone, gamma-butyrolactone, pivalolactone, alpha-hydroxybutryic acid, alpha-hydroxyisobutyric acid, alpha-hydroxyisovaleric acid, alpha-hydroxycaproic acid, alpha-hydroxyisocaproic acid, alpha-hydroxy-alpha-ethylbutyric acid, alpha-hydroxy-alpha-methylvaleric acid, alpha-hydroxyheptanoic acid, alpha-hydroxyoctanoic acid, alpha-hydroxydecanoic acid, alpha-hydroxytetradecanoic acid, alph-hydroxystearic acid and alpha-hydroxyvaleric acid.

22. The process as claimed in claim 21, further characterized in that the resorbable polyester is and copolymers based on glycolide, lactide, methylglycolide, dimethylglycolide, polymethylglycolide, diethylglycolide, dibutylglycolide, caprolactone, valerolactone, decalactone, propiolactone, butyrolactone and pivalolactone.

23. The process as claimed in claim 21, further characterized in that the resorbable polyester is selected from the group of a copolymer of D,L-lactide and glycolide with inherent viscosities of at least 2.5 dl/g, corresponding to average molecular weights of at least 110,000, a copolymer of e-caprolactone with L-, D,L-lactide and glycolide and inherent viscosities of up to at least 4 dl/g; poly(L-lactide-co-D,L-lactide) in the ratio 9:1, poly(L-lactide-co-glycolide) in the ratio 7:3, poly(D,L-lactide-co-glycolide) in the ratio 3:1, poly(D,L-lactide-co-glycolide) in the ratio 1:1 and poly(D,L-lactide-co-glycolide) in the ratio 45:55.

* * * * *